United States Patent [19]

Matsushima et al.

[11] 4,169,941
[45] Oct. 2, 1979

[54] DERIVATIVES OF XK-88-5 AND PROCESS FOR THE PRODUCTION THEREOF

[75] Inventors: Hideo Matsushima, Machida; Yasuki Mori, Kawasaki, both of Japan

[73] Assignee: Abbott Laboratories, North Chicago, Ill.

[21] Appl. No.: 863,629

[22] Filed: Dec. 23, 1977

[30] Foreign Application Priority Data

Dec. 25, 1976 [JP] Japan ................. 51-155656

[51] Int. Cl.$^2$ ............................................ C07H 15/22
[52] U.S. Cl. ..................................... 536/17 R; 536/4
[58] Field of Search ........................................ 536/17

[56] References Cited
U.S. PATENT DOCUMENTS

| | | | |
|---|---|---|---|
| 3,997,524 | 12/1976 | Nagabhushan | 536/17 |
| 4,000,262 | 12/1976 | Daniels | 536/17 |
| 4,002,608 | 1/1977 | Wright et al. | 536/17 |
| 4,029,882 | 6/1977 | Wright | 536/17 |
| 4,053,591 | 10/1977 | Daniels et al. | 536/17 |

Primary Examiner—Johnnie R. Brown
Attorney, Agent, or Firm—Fitzpatrick, Cella, Harper & Scinto

[57] ABSTRACT

A new compound which is useful as an antibacterial agent or a synthetic intermediate thereof and has the general formula:

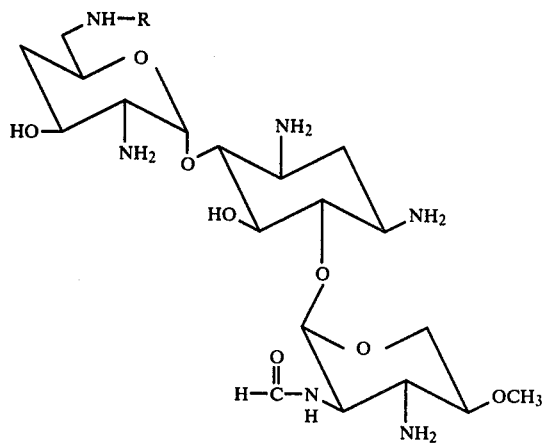

(wherein R is hydrogen, benzyloxycarbonyl or t-butyloxycarbonyl) is produced by reacting the compound XK-88-5 with an urethane-type amino-protecting reagent.

1 Claim, 2 Drawing Figures

DERIVATIVES OF XK-88-5 AND PROCESS FOR THE PRODUCTION THEREOF

BACKGROUND OF THE INVENTION

The present invention relates to new derivatives of the compound XK-88-5 and a process for the production thereof.

XK-88-5 is one factor of a series of related antibiotic compounds, XK-88 series of antibiotics, produced by culturing a microorganism belonging to the genus Streptomyces. XK-88-5 and the fermentative production thereof are disclosed in U.S. Pat. No. 3,939,043 issued Feb. 17, 1977. The XK-88 series of antibiotics are also known as seldomycins. XK-88-5 (seldomycin factor-5) exhibits a high antibacterial activity. New semi-synthetic derivatives of XK-88-5 would, therefore, be useful as antibacterial agents. However, since XK-88-5 represented by the formula:

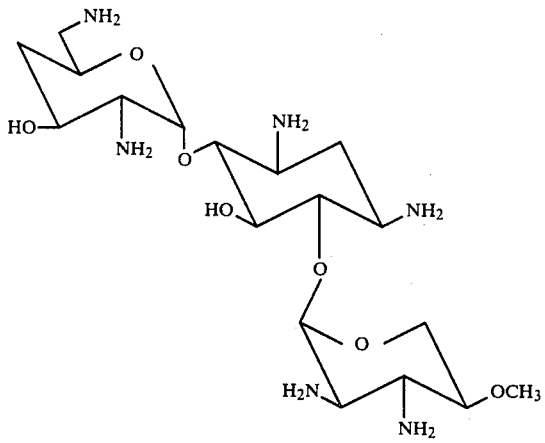

has six primary amino groups in the molecule, it is difficult to introduce a substituent into a specific amino group in order to prepare new derivatives. Therefore, it is very desirable to provide a method of protecting a particular amino group in the molecule of XK-88-5 and to provide a derivative of XK-88-5 having a protected amino group at a particular position.

It is well known that when an aminoglycoside antibiotic is reacted with an amino-protecting reagent, the amino group at the 6'-position is readily protected with the amino-protecting group.

It has been found that, when XK-88-5 is reacted with an urethane-type amino-protecting reagent, the amino group at the 2"-position of XK-88-5 is selectively formylated. In that case the amino group at the 6'-position may be simultaneously protected or not protected.

As a conventional method of formylating an amino group, a method using ethyl formate or a mixture of formic acid and acetic anhydride is known. The known method is described in "Protective Groups in Organic Chemistry" pages 46–49, (Plenum Press, 1973). According to the known method, most of the amino groups are formylated and it is impossible to formylate a particular amino group of XK-88-5 selectively. For example, Japanese Unexamined Patent Publication No. 35129/75 discloses a method in which an aminoglycoside antibiotic having a deoxystreptamine ring is reacted with a mixture of formic acid and acetic anhydride or with active esters of formic acid such as p-nitrophenylformate, and all amino groups of the antibiotic are formylated.

BRIEF DESCRIPTION OF DRAWINGS

In FIG. 1, the signal indicated by the sign "x" means spin noise on the measuring apparatus. Spectrum in the upper part of FIG. 1 is a part of $^1$H-NMR spectrum obtained when the abscissa is graduated with twofold scale.

SUMMARY OF THE INVENTION

Figure 1:
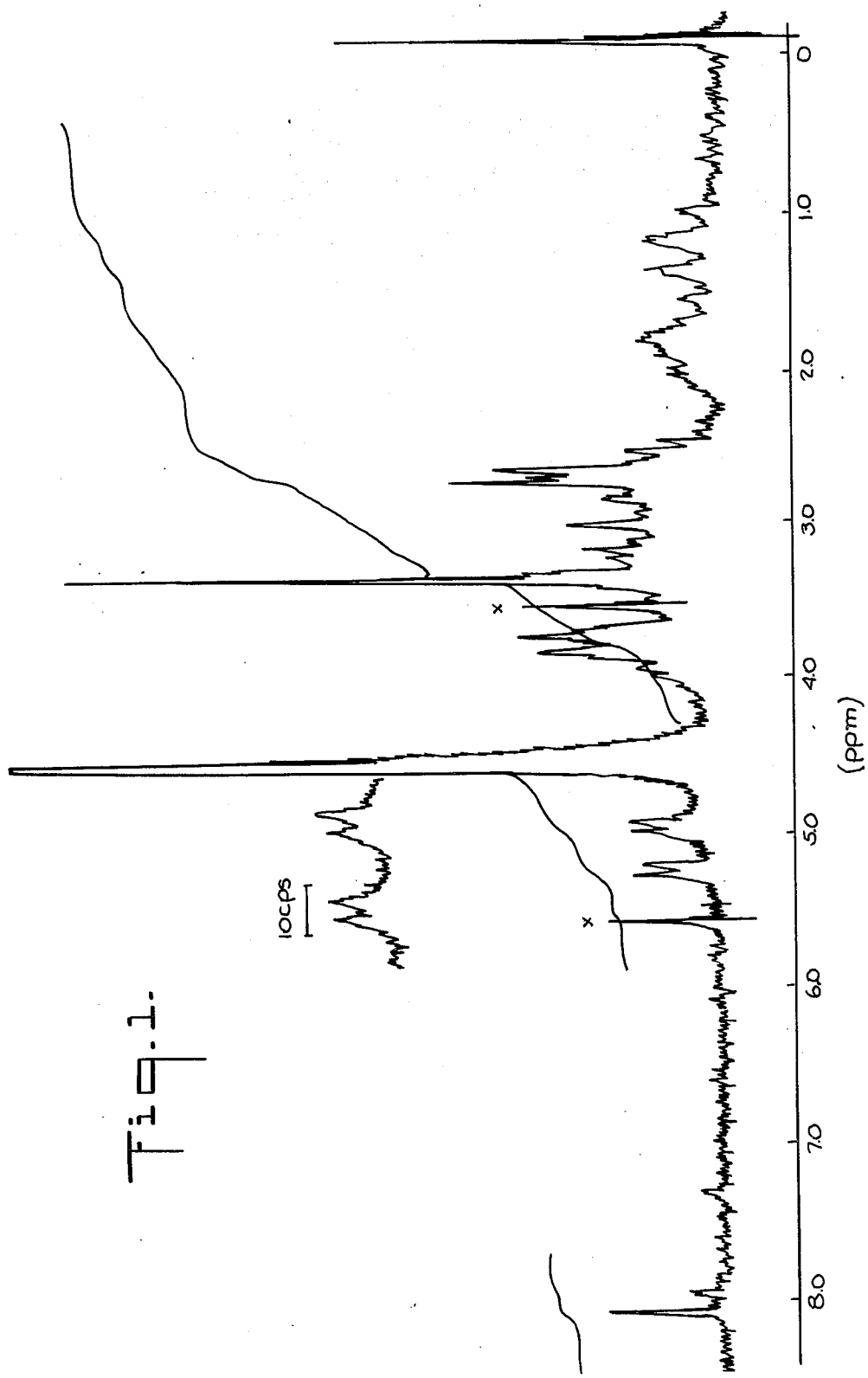
FIG. 1 illustrates $^1$H-NMR spectrum of 2"-N-formyl XK-88-5 measured in deuterium oxide.

The present invention relates to new derivatives of XK-88-5 having the general formula:

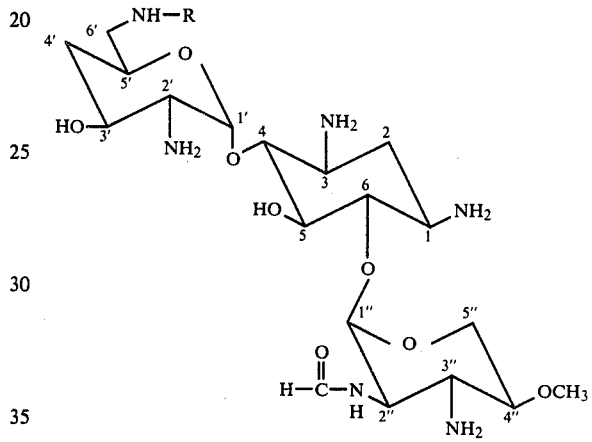

(wherein R is hydrogen, benzyloxycarbonyl or t-butyloxycarbonyl), and a process for the production thereof.

Since a specific amino group of the desired products is protected with an amino-protecting group, the desired products are useful as intermediates for the synthesis of a novel derivative of XK-88-5. Moreover, one of the desired products, 2"-N-formyl-XK-88-5 exhibits a strong antibacterial activity, and is useful as an antibacterial agent.

Included in the composition of matter aspect of the invention are the pharmaceutically acceptable, non-toxic acid addition salts of 2"-N-formyl-XK-88-5.

According to the present invention, the desired products are obtained by reacting XK-88-5 with an urethane-type amino-protecting reagent to selectively formylate the amino group at the 2"-position of XK-88-5.

DETAILED DESCRIPTION OF THE INVENTION

The compounds of the present invention are produced by reacting XK-88-5 with an urethane-type amino-protecting reagent in a suitable solvent.

As preferable urethane-type amino-protecting reagents, benzyloxycarbonylchloride, N-benzyloxycarbonyloxysuccinimide, benzyl pentachlorophenylcarbonate, t-butyloxycarbonylazide and t-butyl S-4,6-dimethylpyrimidin-2-ylthiolcarbonate may be used. These amino-protecting reagents are mentioned in "Protective Groups in Organic Chemistry" pages 56–60 (Plenum Press, 1973).

The urethane-type amino-protecting reagent is used in an amount of 0.1 to 10 mol, preferably, 0.3 to 3.0 mol per one mol of XK-88-5. In the reaction mixture, the preferable concentration of XK-88-5 is 0.001 to 1.0 M and that of the urethane-type amino-protecting reagent is 0.001 to 10 M.

A solvent suitable for the reaction may be at least one selected from the group consisting of dioxane, tetrahydrofuran, ethylene glycol dimethyl ether, N,N-dimethylformamide, dimethylsulfoxide, methanol, ethanol, propanol, water, acetone, acetonitrile and pyridine. A mixed solvent of water and organic solvent (1:0.1 to 10 by volume) is especially preferred.

The reaction is carried out at a temperature of $-20°$ to $50°$ C., preferably, $-10°$ to $30°$ C. for 0.5 to 48 hours, preferably, 1 to 24 hours.

After the completion of the reaction, the product may be isolated and purified from the reaction mixture by ion-exchange chromatography, silica gel chromatography, etc.

The methods for the production of the acid addition salts are well known in the art.

The present compounds are useful as intermediates to prepare further novel derivatives of XK-88-5.

Among the compounds of the present invention, 2''-N-formyl-XK-88-5 is useful as an antibiotic due to the antibacterial activity thereof. The fact that an N-formylated derivative of an aminoglycoside antibiotic has an excellent antibacterial activity is a novel finding of the present inventors.

The following Table 1 illustrates minimum inhibitory concentrations (MIC) of 2''-N-formyl-XK-88-5 against various Gram-positive and Gram-negative bacteria determined by agar dilution method (pH 8.0).

Table 1

| Microorganisms | MIC (γ/ml) |
| --- | --- |
| *Vibrio percolans* KY 4174 | 10.0 |
| *Pseudomonas alkaligenes* KY 4656 | 2.50 |
| *Erwinia aroideae* KY 3241 | 1.25 |
| *Staphylococcus aureus* Ky 4279 | 0.32 |
| *Escherichia coli* KY 4271 | 2.50 |
| *Bacillus subtilis* KY 4273 | 0.32 |
| *Proteus vulgaris* KY 4277 | 2.50 |
| *Shigella sonnei* KY 4281 | 2.50 |
| *Salmonella typhosa* KY 4278 | 2.50 |
| *Klebsiella pheumoniae* KY 4275 | 0.64 |

This compound of the present invention is, therefore, useful as an antibacterial agent to clean and disinfect laboratory glassware and surgical instruments, and may also be used for pharmaceutical and sanitation purposes in cleaning and sanitizing hospital rooms and areas.

Non-toxic acid addition salts of the present compound also have as broad an antibacterial spectrum as the free base of the present compound, and the similar effects can be expected.

Herein the non-toxic acid addition salts mean mono-, di-, tri-, tetra- and penta-salts, which are formed by reaction of one molecule of 2''-N-formyl-XK-88-5 with 1 to 5 molecules of pharmaceutically acceptable non-toxic acid. Those pharmaceutically acceptable non-toxic acids include inorganic acids such as sulfuric acid, hydrochloric acid, hydrobromic acid, hydriodic acid, phosphoric acid, carbonic acid, nitric acid, etc., and organic acids such as acetic acid, fumaric acid, maleic acid, malic acid, citric acid, succinic acid, mandelic acid, ascorbic acid, tartaric acid, etc. and amino acids such as aspartic acids, etc.

One of the novel intermediates of the present invention, 6'-N-benzyloxycarbonyl-2''-N-formyl-XK-88-5 is converted to 2''-N-formyl-XK-88-5 by eliminating benzyloxycarbonyl group at the 6'-position by hydrogenolyzation. Further, the other intermediate 6'-N-t-butyloxycarbonyl-2''-N-formyl-XK-88-5 is converted to 2''-N-formyl-XK-88-5 by eliminating t-butyloxycarbonyl group at the 6'-position by the treatment with acids such as trichloroacetic acid and hydrochloric acid. Therefore, 6'-N-benzyloxycarbonyl-2''-N-formyl-XK-88-5 and 6'-N-t-butyloxycarbonyl-2''-N-formyl-XK-88-5 are useful as an intermediate for the production of 2''-N-formyl-XK-88-5.

EXAMPLE 1

Preparation of 2''-N-formyl-XK-88-5

In this example, 5 g (11.6 mmol) of XK-88-5 (free base) is dissolved in a mixed solvent of 190 ml of water and 160 ml of ethylene glycol dimethyl ether. Separately, 3.09 g of N-benzyloxycarbonyloxysuccinimide is dissolved in 30 ml of ethylene glycol dimethyl ether and the solution is cooled in an ice-bath. The cooled solution is then added dropwise to the solution of XK-88-5 over a period of 20 minutes with stirring under ice-cooling. The resultant mixture is stirred for 3 hours in the ice-bath and then allowed to stand at $5°$ C. for 15 hours. A small amount of precipitate formed is removed by filtration and the filtrate is concentrated to dryness under reduced pressure. To the residue is added 60 ml of water and the insoluble matter is removed by filtration. The filtrate is adjusted to pH 4.4 with concentrated hydrochloric acid and then charged into a column packed with 500 ml of Amberlite CG-50 ($NH_4^+$ form) (trademark for a weakly acidic cation exchange resin produced by Rohm & Haas Co., U.S.A.). Washing and elution are carried out by passing 1500 ml of water, 2240 ml of 0.1 N aqueous ammonia, 730 ml of 0.15 N aqueous ammonia and 1430 ml of 0.3 N aqueous ammonia through the column in turn. After 1500 ml of water and are ml of 0.1 N aqueous ammonia are passed, the eluate is taken in 22 ml portions while checking the components of the eluate by thin layer chromatography. Fraction Nos. 45–87 are combined and concentrated to dryness under reduced pressure to obtain 4.1 g of pale yellow powder. This powder is ascertained to contain 6'-N-benzyloxycarbonyl-XK-88-5 and 6'-N-benzyloxycarbonyl-2''-N-formyl-XK-88-5. Fraction Nos. 102–135 alre combined and concentrated to dryness under reduced pressure to obtain 0.325 g (0.71 mmol) of basic white powder. This powder has the following physicochemical properties.

Melting point: $136°$–$147°$ C.

Specific rotation: $[\alpha]_D^{21} = +104°$ (c=0.300, water)

Elementary analysis (%): Calculated for $C_{19}H_{38}N_6O_8 \cdot H_2O$: C=45.95, H=8.13, N=16.93. Found: C=45.85, H=8.03, N=16.66.

$^1$H-NMR spectrum (ppm):

Shown in FIG. 1.

$^{13}$C-NMR spectrum (ppm) (based on TMS standard):

Obtained by measuring $^{13}$C-NMR spectrum in deuterium oxide using dioxane as an internal standard compound and then converting the values to values based on TMS standard presuming those of dioxane as 67.4 ppm, and shown as follows.

$C_1'$ 101.9, $C_2'$ 57.5, $C_3'$ 68.8, $C_4'$ 36.8, $C_5'$ 70.1, $C_6'$ 45.2, $C_1$ 51.1, $C_2$ 36.4, $C_3$ 50.0, $C_4$ 87.3, $C_5$ 75.2, $C_6$ 87.2, $C_1''$ 97.8, $C_2''$ 53.1, $C_3''$ 52.3, $C_4''$ 80.2, $C_5''$ 60.8, $OCH_3$ 58.9, CHO 165.2.

In the above values, values on $C_4'$ and $C_2$ may be mutually exchangeable, and that is the case with the values on $C_2''$ and $C_3''$.

From the above physicochemical properties the compound is identified as 2''-N-formyl-XK-88-5 (yield 6.08%)

EXAMPLE 2

Preparation of 6'-N-benzyloxycarbonyl-2''-N-formyl-XK-88-5

In this example, 4.10 g of powder obtained by combining Fraction Nos. 45–87 and concentrating it to dryness as described in Example 1 is dissolved in about 25 ml of a mixed solvent consisting of n-butanol, ethanol, chloroform and concentrated aqueous ammonia (4:5:2:1 by volume). The solution is charged into a column packed with 250 g of silica gel. Then, elution is carried out with 1290 ml of the same mixed solvent as described above while checking the components of the eluate by thin layer chromatography and the eluate is taken in 22 ml portions. Fraction Nos. 59–70 are combined and concentrated to dryness under reduced pressure to obtain 0.80 g (1.35 mmol) of basic white powder. This powder has the following physicochemical properties.

Melting point: 124°–127° C.
Specific rotation: $[\alpha]_D^{25} = +101°$ (c=0.382, water)
Elementary analysis (%): Calculated for $C_{27}H_{44}N_6O_{10}.\frac{1}{2}H_2CO_3$: C=51.30, H=7.06, N=13.06. Found: C=51.64, H=7.25, N=12.11.

$^{13}$C-NMR spectrum (ppm) (based on TMS standard):

Obtained by measuring $^{13}$C-NMR spectrum in deuterium oxide using dioxane as an internal standard compound and then converting the values to values on TMS standard presuming those of dioxane as 67.4 ppm and shown as follows.

$C_1'$ 102.7, $C_2'$ 57.5, $C_3'$ 68.7, $C_4'$ 36.5, $C_5'$ 69.4, $C_6'$ 45.2, $C_1$ 50.8, $C_2$ 36.5, $C_3$ 50.0 $C_4$ 89.1, $C_5$ 74.8, $C_6$ 86.9, $C_1''$ 97.7, $C_2''$ 53.0, $C_3''$ 52.2, $C_4''$ 80.1, $C_5''$ 60.7, $OCH_3$ 58.8, benzyl C 67.6, benzyl ring 137.2, 129.6, 128.9, carbonyl group of benzyloxycarbonyl group 158.9, CHO 165.1.

In the above values, values on $C_2''$ and $C_3''$ may be mutually exchangeable.

Figure 2:
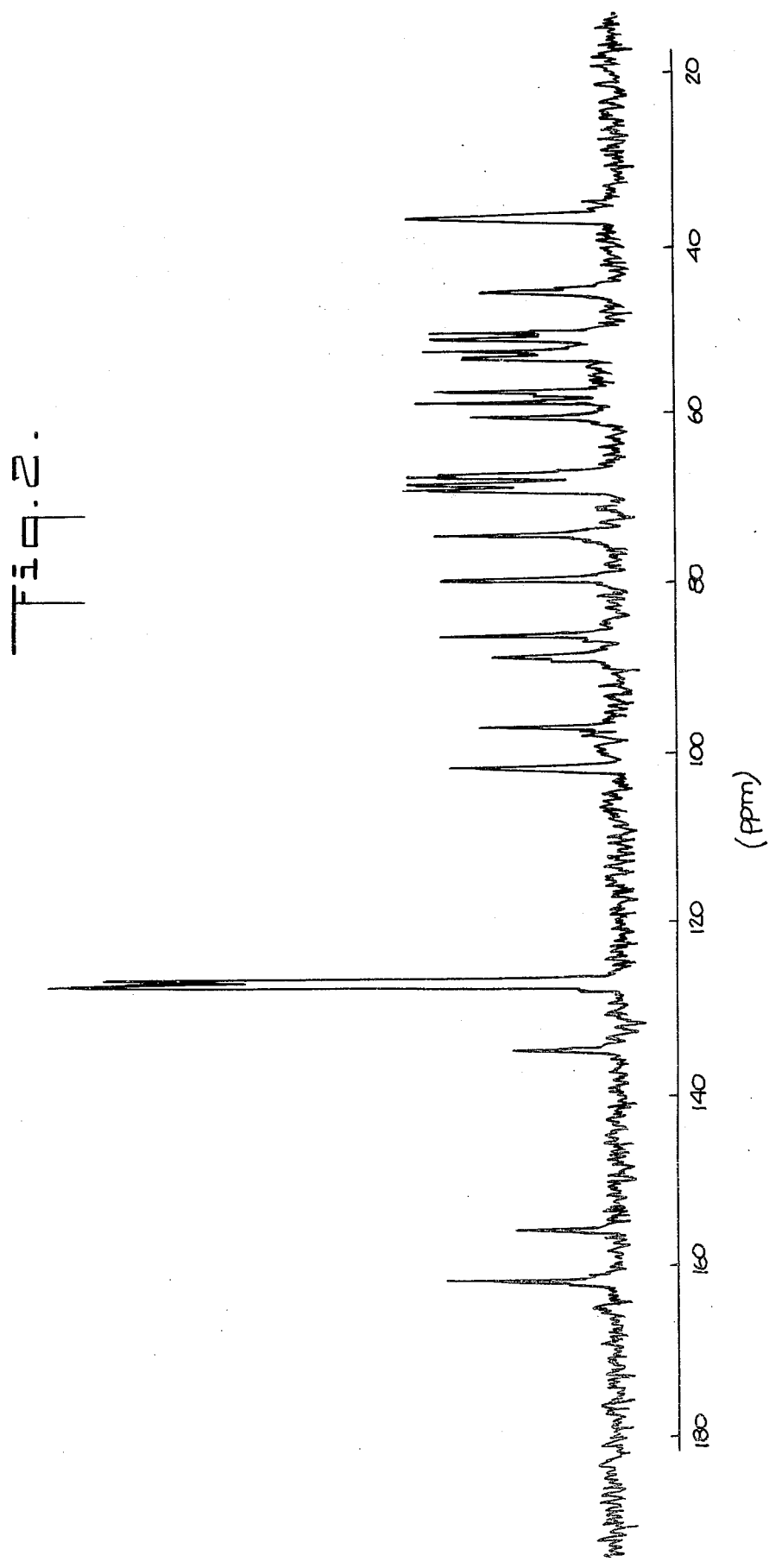
FIG. 2 illustrates $^{13}$C-NMR spectrum of 6'-N-benzyloxycarbonyl-2"-N-formyl-XK-88-5 measured in deuterium oxide.

$^{13}$C-NMR spectrum is also shown in FIG. 2.

From the above physicochemical properties the compound is identified as 6'-N-benzyloxycarbonyl-2''-N-formyl-XK-88-5. (yield 11.6%)

EXAMPLE 3

Preparation of 6'-N-t-butyloxycarbonyl-2''-N-formyl-XK-88-5

In this example, 1.60 g (3.73 mmol) of XK-88-5 (free base) is dissolved in a mixed solvent of 60 ml of water and 45 ml of tetrahydrofuran. Separately, 0.97 g of N-t-butyloxycarbonylsuccinimide is dissolved in 20 ml of tetrahydrofuran and the solution is cooled in an ice-bath. The cooled solution is added dropwise to the above solution of XK-88-5 over a period of 30 minutes with stirring under ice-cooling. The resultant mixture is stirred at 3° C. for 1 hour and then allowed to stand at 5° C. for 21 hours. A small amount of precipitate formed is removed by filtration and the filtrate is concentrated to dryness under reduced pressure. To the residue is added 50 ml of water and the insoluble matter is removed by filtration. The filtrate is adjusted to pH 5.0 with concentrated hydrochloric acid and then charged into a column packed with 120 ml of Amberlite CG-50 ($NH_4^+$ form). The column is washed with 345 ml of water. Then, elution is carried out with 300 ml of 0.1 N aqueous ammonia and 45 ml of 0.2 N aqueous ammonia while checking the components of the eluate by thin layer chromatography. The eluate is taken in 15 ml portions. Fraction Nos. 23–27 are combined and concentrated to dryness under reduced pressure to obtain 1.45 g of powder. This powder is dissolved in about 5 ml of a mixed solvent consisting of n-butanol, ethanol, chloroform and concentrated aqueous ammonia (4:5:2:1 by volume). The solution is charged into a column packed with 60 g of silica gel. Then, elution is carried out with 672 ml of the same mixed solvent as described above and subsequently 612 ml of a mixed solvent consisting of n-butanol, ethanol, chloroform and concentrated aqueous ammonia (4:5:2:2 by volume) while checking the components of the eluate by thin layer chromatography. The eluate is taken in 12 ml portions. Fraction Nos. 31–38 are combined and concentrated to dryness under reduced pressure to obtain 0.24 g (0.45 mmol) of basic white powder. This powder has the following physicochemical properties.

Melting point: 111°–118° C.
Specific rotation: $[\alpha]_D^{23} = +102°$ (c=0.300, water)
Elementary analysis (%): Calculated for $C_{23}H_{46}N_6O_9.H_2CO_3$: C=47.04, H=7.91, N=13.72. Found: C=46.81, H=7.92, N=13.38.

$^{13}$C-NMR spectrum (ppm) (in deuterium oxide)
$\tau$ 1.85 (singlet, 1H),
$\tau$ 8.57 (singlet, 9H)

From the above physicochemical properties the compound is identified as 6'-N-t-butyloxycarbonyl-2''-N-formyl-XK-88-5 (yield 12.1%). Fraction Nos. 44–49 are combined and concentrated to dryness under reduced pressure to obtain 0.55 g of 6'-N-t-butyloxycarbonyl-XK-88-5 as powder. Further, Fraction Nos. 96–98 are combined and concentrated to dryness under reduced pressure to obtain 0.10 g (0.22 mmol) of 2''-N-formyl-XK-88-5 as powder (yield 5.85%)

A process for the preparation of 2''-N-formyl-XK-88-5 from 6'-N-benzyloxycarbonyl-2''-N-formyl-XK-88-5 or from 6''-N-t-butyloxycarbonyl-2''-N-formyl-XK-88-5 is exemplified by the following reference examples.

EXAMPLE 4

In this example, 4.78 g (10 mmol) of 2''-N-formyl-XK-88-5 is dissolved in 20 ml of water. To the solution is added a solution of 0.98 g (10 mmol) of sulfuric acid in 5.0 ml of water under cooling. After 30 minutes, cold ethanol is added to the solution until precipitation is complete. The white precipitate is separated by filtration to obtain the monosulfate of 2''-N-formyl-XK-88-5.

Reference example 1

Preparation of 2''-N-formyl-XK-88-5 from 6'-N-benzyloxycarbonyl-2''-N-formyl-XK-88-5

In this reference example, 200 mg of 6'-N-benzyloxycarbonyl-2''-N-formyl-XK-88-5 is dissolved in 20 ml of a mixed solvent of water and methanol (1:1 by volume), and 50 mg of 10% palladium carbon and 0.1 ml of acetic acid are added thereto. Reaction is carried out by passing hydrogen gas through the solution for 16 hours with stirring. After the reaction is completed, palladium carbon is removed by filtration and washed with 5 ml of the above mixed solvent. The filtrate and washings are combined and concentrated to dryness under reduced pressure. The residue is dissolved in 3 ml of water and the solution is charged into a column packed with 10 ml of Amberlite CG-50 (NH$_4$+ form). The column is washed with 20 ml of water, and then elution is carried out with 20 ml of 0.5 N aqueous ammonia. The whole eluate (about 20 ml) is concentrated to dryness to obtain 149 mg of white powder. This powder is ascertained to have the same physiochemical properties as 2''-N-formyl-XK-88-5 described above.

Reference example 2

Preparation of 2''-N-formyl-XK-88-5 from 6''-N-t-butyloxycarbonyl-2''-N-formyl-XK-88-5

In this reference example, 200 mg of 6'-N-butyloxycarbonyl-2''-N-formyl-XK-88-5 is dissolved in 5 ml of concentrated trifluoroacetic acid and the solution is allowed to stand at room temperature for 1 hour. The reaction mixture is concentrated to dryness under reduced pressure and the residue is dissolved in 5 ml of water. The solution is charged into a column packed with 10 ml of Amberlite CG-50 (NH$_4$+ form). The column is washed with 20 ml of water, and then elution is carried out with 60 ml of 0.1 N aqueous ammonia and 60 ml of 0.2 N aqueous ammonia while checking the components of the eluate by thin layer chromatography. The eluate is taken in 2 ml portions. Fraction Nos. 42–46 are combined and concentrated to dryness under reduced pressure to obtain 102 mg of white powder. This powder is ascertained to have the same physicochemical properties as 2''-N-formyl-XK-88-5 described above.

What is claimed is:

1. A process for producing a compound having the formula:

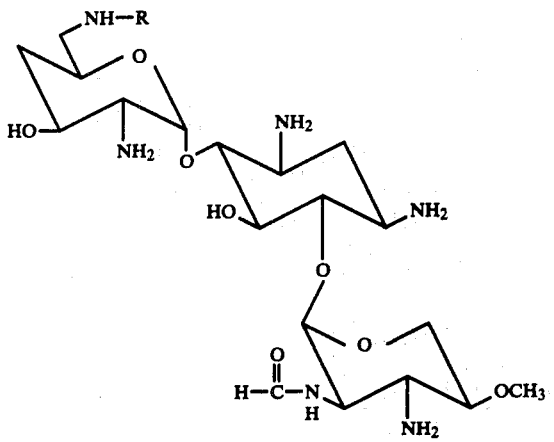

(wherein R is benzyloxycarbonyl or t-butyloxycarbonyl) which comprises reacting the compound XK-88-5 with from 0.1 to 10 mols per mole of XK-88-5 of an urethane-type amino-protecting reagent selected from the group consisting of benzyloxycarbonylchloride, N-benzyloxycarbonyloxysuccinimide, benzyl pentachlorophenylcarbonate, t-butyloxycarbonylazide and t-butyl S-4,6-dimethylprimidin-2-ylthiolcarbonate at a temperature of −20° to 50° C. for 0.5 to 48 hours.

* * * * *

UNITED STATES PATENT AND TRADEMARK OFFICE
CERTIFICATE OF CORRECTION

PATENT NO. : 4,169,941

DATED : October 2, 1979

INVENTOR(S) : HIDEO MATSUSHIMA, et al.

It is certified that error appears in the above–identified patent and that said Letters Patent are hereby corrected as shown below:

Col. 4, line 42, "are" (first occurrence) should be --400--;

line 49, "alre" should be --are--;

Col. 6, line 44, "6"" should be --6'--;

Col. 7, line 15, "6"" should be --6'--.

Signed and Sealed this

Eleventh Day of December 1979

[SEAL]

Attest:

Attesting Officer

SIDNEY A. DIAMOND

Commissioner of Patents and Trademarks